(12) United States Patent
Gumbrecht et al.

(10) Patent No.: US 7,993,828 B2
(45) Date of Patent: Aug. 9, 2011

(54) PCR PROCESS AND ARRANGEMENT FOR DNA AMPLIFICATION USING DRY REAGENTS

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 395 days.

(21) Appl. No.: 11/587,567

(22) PCT Filed: Apr. 26, 2005

(86) PCT No.: PCT/EP2005/051874
§ 371 (c)(1),
(2), (4) Date: Oct. 25, 2006

(87) PCT Pub. No.: WO2005/106023
PCT Pub. Date: Nov. 10, 2005

(65) Prior Publication Data
US 2008/0241890 A1    Oct. 2, 2008

(30) Foreign Application Priority Data
Apr. 30, 2004    (DE) .......................... 10 2004 021 822

(51) Int. Cl.
*C12Q 1/68* (2006.01)
(52) U.S. Cl. ............................................ 435/6
(58) Field of Classification Search .................. None
See application file for complete search history.

(56) References Cited

U.S. PATENT DOCUMENTS

| | | | |
|---|---|---|---|
| 5,411,876 A * | 5/1995 | Bloch et al. .................... | 435/91.2 |
| 5,498,392 A * | 3/1996 | Wilding et al. ............... | 422/68.1 |
| 5,550,044 A | 8/1996 | Kosak et al. | |
| 5,599,660 A | 2/1997 | Ramanujam et al. | |
| 5,783,148 A * | 7/1998 | Cottingham et al. ............ | 422/56 |
| 5,830,644 A | 11/1998 | West et al. | |
| 5,955,351 A | 9/1999 | Gerdes et al. | |
| 5,972,386 A | 10/1999 | Burgoyne | |
| 6,168,948 B1 * | 1/2001 | Anderson et al. .......... | 435/287.2 |
| 6,221,584 B1 | 4/2001 | Emrich et al. | |
| 6,361,958 B1 | 3/2002 | Shieh et al. | |
| 6,403,339 B1 | 6/2002 | Bertling | |
| 6,544,734 B1 | 4/2003 | Briscoe et al. | |
| 6,617,136 B2 * | 9/2003 | Parthasarathy et al. ...... | 435/91.1 |
| 2001/0012612 A1 | 8/2001 | Petersen et al. | |
| 2002/0022261 A1 | 2/2002 | Anderson et al. | |
| 2002/0045246 A1 | 4/2002 | McMillan et al. | |
| 2002/0106686 A1 | 8/2002 | McKernan | |
| 2003/0073110 A1 | 4/2003 | Masaharu et al. | |
| 2004/0018611 A1 | 1/2004 | Ward et al. | |
| 2004/0063197 A1 | 4/2004 | Tilles et al. | |
| 2004/0063198 A1 | 4/2004 | Tilles et al. | |
| 2004/0115094 A1 | 6/2004 | Gumbrecht et al. | |
| 2004/0209354 A1 | 10/2004 | Mathies et al. | |
| 2006/0124895 A1 | 6/2006 | Feucht et al. | |
| 2007/0219366 A1 | 9/2007 | Gumbrecht et al. | |

FOREIGN PATENT DOCUMENTS

| | | |
|---|---|---|
| DE | 102 36 460 A1 | 2/2004 |
| DE | 10236460 | 2/2004 |
| EP | 0 572 057 A | 12/1993 |
| EP | 0572057 | 12/1993 |
| WO | WO 95/06652 | 3/1995 |
| WO | 96/00301 | 1/1996 |
| WO | WO 96/00301 A | 1/1996 |
| WO | WO 9600301 A1 * | 1/1996 |
| WO | 99/33559 | 7/1999 |
| WO | WO 99/33559 A | 7/1999 |
| WO | 02/072262 | 9/2002 |
| WO | WO 02/072262 | 9/2002 |
| WO | WO 02/072262 A | 9/2002 |
| WO | WO 2004/065010 | 8/2004 |

OTHER PUBLICATIONS

Blair P. et al: Wax-embedded PCR reagents;, PR Methods & Applications, Cold Spring Harbor Laboratory Press, US, Bd. 4, Nr. 3, Jan. 12, 1994, S. 191-194, XP000484537.
Kaijalainen S. et al: "An alternative hot start technique for PCR in small volumes using beads of Wax-embedded reaction components dried in trehalose"; Nucleic acids research, Oxford university press, Surrey, GB, Bd. 21, Nr. 12, 1993, S. 2959-2960, XP002027157.
Dale S.J.: "Direct microtiter plate sequencing of PCR-amplified M13 clones from plaques using dried reagents"; Biotechniques, Feb. 1992, Bd. 12, Nr. 2, S. 194, 196-197, XP009052693.
McMillan W.A.: "Rapid real-time PCR with fully integrated specimen preparation"; Phytopathology, St Paul, MN, US, Bd. 92, Nr. 6, Suppl, Jul. 27, 2002, S. 110. XP008044514.
Raja Siva et al.: "Technology for automated, rapid, and quantitative PCR or reverse transcription-PCR clinical testing"; Clinical Chemistry. Mai 2005, Bd. 51, Nr. 5, Mar. 3, 2005, S. 882-890, XP001207245.

(Continued)

*Primary Examiner* — Christopher M. Babic
(74) *Attorney, Agent, or Firm* — Harness, Dickey & Pierce, P.L.C.

(57) ABSTRACT

A PCR process for DNA amplification with thermocyclisation of the corresponding reagents is disclosed, in which total integration of all substances and process steps is achieved in a closed, single-use unit (so-called cartridge) in which the reagents are stored in a storage-stable form at room temperature. According to the process, the water-soluble reagents are covered by a water-insoluble medium, then the DNA to be amplified is supplied and the water-insoluble medium is eliminated, so that the water-soluble reagents are dissolved and PCR can start. In the corresponding arrangement, a test unit designed as a single-use produce (a so-called cartridge) has at least one micro-channel or micro-cavity for receiving a PCR reagent. The PCR reagents in the form of a mixture which can be dried at a negligible vapour pressure and forms a storage-stable substance substance at room temperature adhere to the walls of the micro-channel or micro-cavity and form a thin film covered by an insoluble medium.

15 Claims, 4 Drawing Sheets

OTHER PUBLICATIONS

International Search Report.

International Search Report (PCT/ISA/210) Aug. 22, 2005.

"Wax Embedded PCR Reagents". Blair et al. PCR Methods & Applications, Cold Spring Harbor Laboratory Press, US, vol. 4, No. 3, Dec. 1, 1994, pp. 191-194.

"An Alternative Hot Start Technique for PCR in Small Volumes Using Beads of Wax-Embedded Reaction Components Dried in Trehalose". Kaijalainen et al. Nucleic Acids Research, Oxford University Press, Surrey, GB, vol. 21, No. 12, 1993, pp. 2959-2960.

"Direct Microtiter Plate Sequencing of PCR-amplified M13 Clones from Plaques Using Dried Reagents". Dale. Biotechniques, Feb. 1992, vol. 12, No. 2, pp. 194, 196-197.

"Rapid Real-Time PCR with Fully Intergrated Specimen Preparation". McMillan. Phytopathology, St. Paul, MN, US, vol. 92, No. 6, Suppl, Jul. 27, 2002, p. S110.

Technology for Automated, Rapid, and Quantitative PCR or Reverse Transcription-PCR Clinical Testing. Raja et al. Clinical Chemistry, vol. 51, No. 5, Mar. 3, 2005, pp. 882-890.

Office Action mailed Oct. 16, 2009 for U.S. Appl. No. 11/587,581.

* cited by examiner

PCR PROCESS AND ARRANGEMENT FOR DNA AMPLIFICATION USING DRY REAGENTS

PRIORITY STATEMENT

This application is the national phase under 35 U.S.C. §371 of PCT International Application No. PCT/EP2005/051874 which has an International filing date of Apr. 26, 2005, which designated the United States of America and which claims priority on German Patent Application number 10 2004 021 822.6 filed Apr. 30, 2004, the entire contents of which are hereby incorporated herein by reference.

FIELD

The invention generally relates to a process for DNA amplification. For example, it relates to a process for DNA amplification by PCR with thermocycling of the substances containing the DNA together with the associated reagents. The invention also generally relates to an associated arrangement for carrying out the process.

BACKGROUND

For the nucleic acid analysis e.g. of white blood cells from whole blood to answer human genomic questions, the cells must firstly be broken up in a sample preparation step and the DNAs thereby released must subsequently be isolated. It is in this case necessary to remove blood constituents such as hemoglobin, immunoglobulins and lactoferrin, which could inhibit a subsequent PCR.

In the laboratory, these working steps are carried out according to a sufficiently well-known prior art. In particular, the DNAs are bound to so-called magnet beads for isolation. The magnet beads with the DNA can be transported in a controlled way via external magnetic fields and enriched at predetermined positions. The isolated DNA can subsequently be eluted from the beads or used together with the beads (as a DNA/bead complex) for the PCR (Polymerase Chain Reaction).

According to the prior art, the isolated genomic DNA is added to a PCR reagent solution (polymerase, primer, nucleotides, buffer, auxiliaries) and the entire batch is subjected to thermocycling which is suitable for the PCR.

Conduct of the latter process is contingent on the provision of laboratory equipment such as PCR equipment (thermocycler), so-called Eppendorf reaction vessels, pipetting equipment, cooling containers for reagents, and must be carried out by trained personnel while complying with safety rules (infection risk, waste disposal . . . ). A plurality of volumetric, accurate dosings (pipettings) of reagent solutions must be carried out. These working steps are also time-consuming.

EP 0 572 057 A1 discloses a composition for PCR reagents, in which the reagents are covered with a meltable material in order to prevent undesired reactions. The way in which false reactions can be avoided before the PCR per se is furthermore described in detail by the publication in "Nucleic Acids Research", Vol. 20, No. 7, pages 1717 to 1723. So-called hot-start PCR, which is based on an elevated starting temperature, is moreover described in [www.bioexpress.com].

The processes described above are suitable in principle for laboratory analysis. U.S. 2002/0022261 A1 moreover describes a system for miniaturized genetic analysis and associated operating processes, in which a cartridge with at least one input to a channel is used. Disintegration of cells for a subsequent PCR is intended to take place in the channel. For the PCR, reagents relevant thereto are provided.

DNA analysis devices are known from WO 02/072262 A1, U.S. Pat. No. 5,550,044 A, U.S. Pat. No. 5,599,660 A and U.S. Pat. No. 5,972,386 A. PCR methods are furthermore described in the publications PCR Met. Appl. Vol. 4, No. 3, pages 191 to 194 and Nucl. Acid Research Res., Vol. 21, pages 2959 to 2960.

SUMMARY

In at least one embodiment of the invention, the PCR reaction is performed in an integrated miniaturized cartridge and an arrangement suitable therefore is provided.

The invention is based on WO 02/0072262 A1 entitled "Analysis Device". This has already described the use of dryly stored, room-temperature stable reagents in microchannels or microcavities of a "chip card", which are put into solution by supplying water shortly before use. This prior art entails providing the dry reagents in a pre-portioned form, so that a quantitative analysis medium is obtained after dissolving. At least one embodiment of the present invention, on the other hand, involves PCR for the purpose of subsequent analysis, for which cell disintegration with isolation of DNA particularly from a whole blood sample must be carried out beforehand.

At least one embodiment of the invention achieves at least one of the following advantages compared with the laboratory method:
  all the materials and processes are fully integrated in a closed single-use cartridge;
  the reagents are held in a form which is stable when stored at room temperature;
  no manual working steps are necessary, other than injection of the DNA to be amplified or the blood sample when integrating cell disintegration and PCR;
  no direct contact takes place with materials that are hazardous to health since blood, reagents and reagent waste remain in the cartridge;
  a compact cartridge geometry allows efficient and rapid thermocycling;
  the cartridge is inexpensive to produce.

When PCR reagents are pre-dosed in dried form, then defined dosing of liquid in respect of volume and composition is to be ensured since the quality and quantity of the PCR reaction depend crucially on these parameters. Without thorough mixing, liquid flowing through a channel coated with dry reagent could lead to a false concentration of the reagents.

For DNA bound in biological structures, for example cells, at least one embodiment of the invention advantageously makes it possible to disintegrate the structure with isolation of the DNA before the PCR reaction. With cell disintegration, in particular, whole blood samples can now be processed directly. Particularly when e.g. magnet bead-bound DNAs from whole blood cell disintegration are to be used for the PCR, it is necessary to remove PCR-inhibiting materials from the sample. This may be done particularly advantageously by fixing the magnet beads by a magnetic field in the PCR chamber and washing the beads. When dry PCR reagents are used, it is necessary to provide means which prevent these reagents from dissolving during the wash process. This is done according to at least one embodiment of the invention by introducing a protective layer, e.g. paraffin.

In a self-inventive refinement, array arrangements could be used for the PCR reaction in at least one embodiment of the invention. This makes it possible to carry out studies on various DNA target sequences simultaneously, which offers a significant time saving.

An arrangement according to at least one embodiment of the invention comprises the following features:

at least one microchannel or microcavity is provided.

The PCR reagent, in at least one embodiment, introduced in the microchannel, or preferably in the microcavity, has the following properties:

the dryable substances have a negligible vapor pressure;
the property that a PCR can be carried out is preserved in the substances which are stable when stored at room temperature;
the substance mixture adheres to microchannel or microcavity walls;
the substance mixture forms a thin film;
the substance mixture is covered water-tightly with an aqueous-insoluble medium, in particular a thin paraffin layer.

Especially in combination with cell disintegration from whole blood, in at least one embodiment, the following properties are obtained for the lysis reagent introduced into the microcavity or preferably in the microchannel:

lysis properties are provided for white blood cells and/or other cells bacteria or viruses;
dryable substances with a negligible vapor pressure are likewise used;
the cell disintegration properties are preserved in the substances which are stable;
the substance mixture adheres to microchannel or microcavity walls;
the "lysis channel" opens in the PCR cavity.

BRIEF DESCRIPTION OF THE DRAWINGS

Further details and advantages of the invention will be found in the following description of example embodiments with the aid of the drawings in conjunction with the patent claims.

DETAILED DESCRIPTION OF THE EXAMPLE EMBODIMENTS

Figure 1:
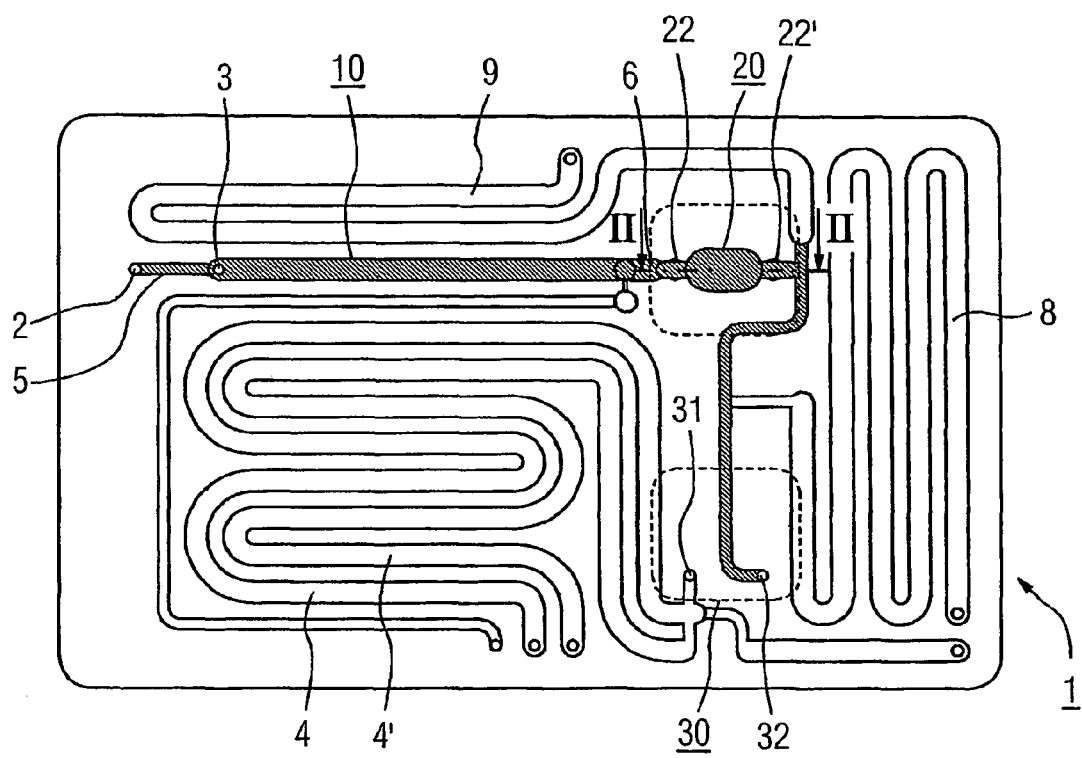
FIG. 1 shows a plan view of an analysis device.

FIG. 1 represents an analysis device, which may be designed as a central or decentral measuring device. In particular, the analysis device is designed in the manner of a chip card ("lab-on-a-chip"), which contains all the devices/methods for treating and evaluating measurement samples.

For example, the device includes a card 1 which includes inlets and outlets. In particular, an inlet (port) 2 is provided for introducing water and an inlet 3 (port) is provided for introducing a measurement sample, for example blood. What is essential is that measurement samples, on the one hand, and solvents, on the other hand, are combined via suitable fluidic devices 2 to 10 and, after isolation of the DNAs contained in the measurement sample, the latter are supplied to a PCR chamber.

Besides the aforementioned water and sample ports 2, 3, the fluidic devices specifically contain two reagent channels 4, 4' as well as a flow channel 5 with an outlet 6, a reception channel 8 for waste and a further fluidic channel 9. A central mixing region in the flow channel 5 for the sample preparation is denoted by 10.

Besides the PCR chamber, the card 1 ("cartridge") furthermore contains a detection module 30 with associated connections for signal processing. Devices/passageways for receiving the residues are furthermore provided. This ensures an integration in which no substances hazardous to health can escape.

The disintegration of a whole blood sample will be described in detail with the aid of the parallel patent application in the name of the Applicant with the same application priority entitled "Method and assembly for DNA isolation with dry reagents". FIGS. 2 to 5 serve to illustrate how in detail the preparations for a DNA amplification are carried out:

A cavity 20 is provided, in which a PCR reaction takes place. PCR (Polymerase Chain Reaction) amplification is sufficiently well known from the prior art. Specifically, thermocycling takes place according to a predetermined temperature program.

Figure 2:
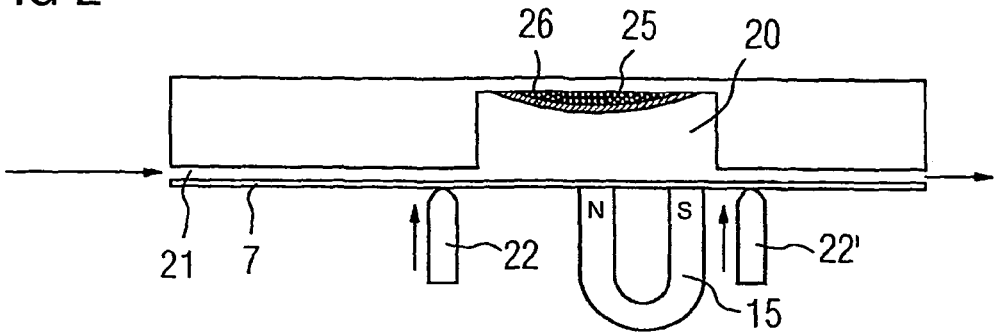
FIG. 2 to FIG. 5 respectively show a detail of FIG. 1 in longitudinal section along the line II-II to illustrate the PCR preparation, the individual Sub-FIGS. 2 to 5 respectively representing different function steps.

In FIG. 2, after the cell disintegration, the measurement sample travels via a flow channel 21 into the PCR cavity 20. A storage-stable and runtime-stable PCR dry reagent 25 is stored in the PCR cavity 20. The term storage-stable/long-term-stable solid in this context is intended to mean that the solid is stored for at least several months at room temperature in this context while preserving the property of inducing PCR.

The dry reagent 25 is water-soluble and must be protected against dissolving and denaturing e.g. by the disintegration reagents before the PCR reaction per se, i.e. at the stage of the sample preparation and washing. To this end, there is an aqueous-insoluble medium 26 on top of the reagent 25. In particular, a paraffin layer may be employed for this purpose.

It is true that the separation of two liquids with the aid of a solidified paraffin separating layer, with the aim of combining the two liquids by melting the paraffin, is already known. It is used particularly in conventional so-called "hot-start" PCR. In the present case, however, it is not a liquid but a solid which is coated with paraffin.

Figure 3:
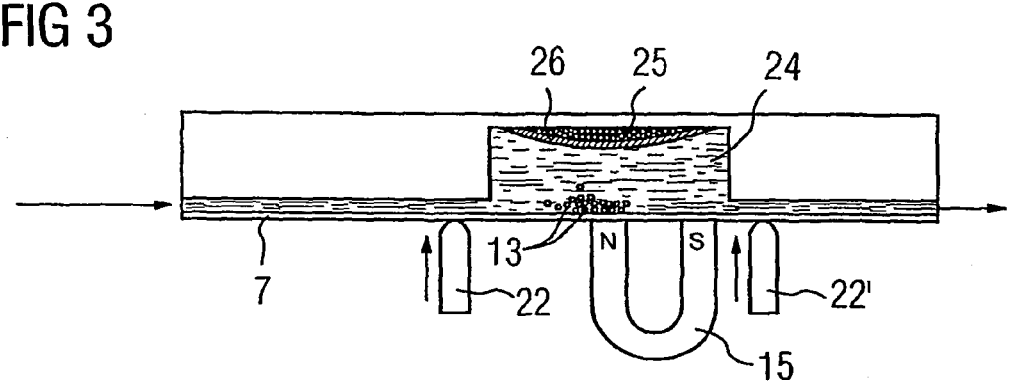

Furthermore, valves 22, 22' and a magnet 15 are functionally indicated in FIG. 2. Their function will be explained below in the further substeps of FIGS. 3 to 5:

It can be seen from FIG. 3 that when the valves 22, 22' are open, the measurement solution with the DNA bound via the magnet beads 12 enter the measurement cavity 20. The DNA is concentrated on the relevant magnet pole via the magnet action. At this stage a washing process may firstly be carried out, the valves 22, 22' being closed after the washing.

Figure 4:
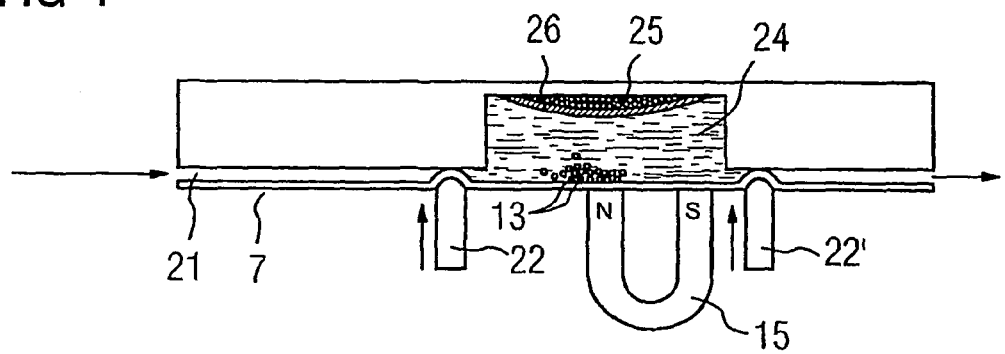
Figure 5:
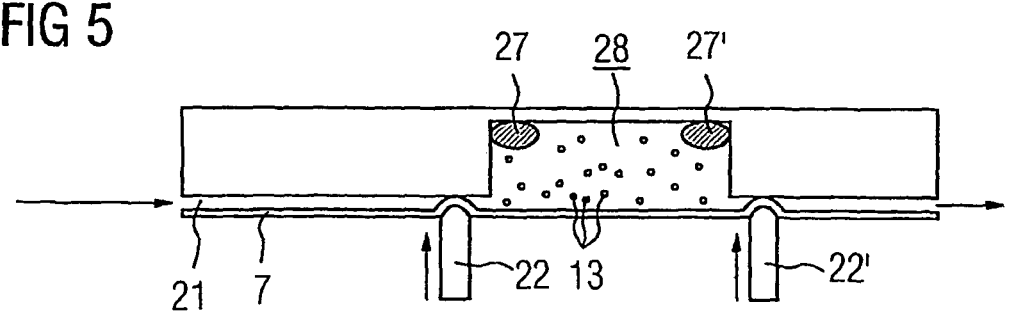

The PCR cavity 20 closed according to FIG. 4 now contains the reagent 25, the cover layer 26 and the aqueous solution 24 with the concentrated DNA. The PCR reaction per se subsequently begins. Upon first heating according to the PCR thermocycling, the paraffin layer 26 is melted according to FIG. 5 and separated into small balls 27, 27'. The PCR reagent 25, on the other hand, is dissolved with suitable dosing in the solvent or in the buffer solution 24. The PCR cavity 20 then contains the concentrated DNA bound to the magnet bead 13 as a suspension 28. The PCR can now be carried out by repeated execution of a thermocycling program.

For the solid provided as a PCR reagent in FIGS. 2 to 5, it is important to select a substance with a negligible vapor pressure, which is stable when stored at room temperature. The substance may be a substance mixture. What is essential is that it is longterm-stable in a pre-dosed form, i.e. retains its properties over several months so that the PCR reaction can be carried out.

Figure 6:
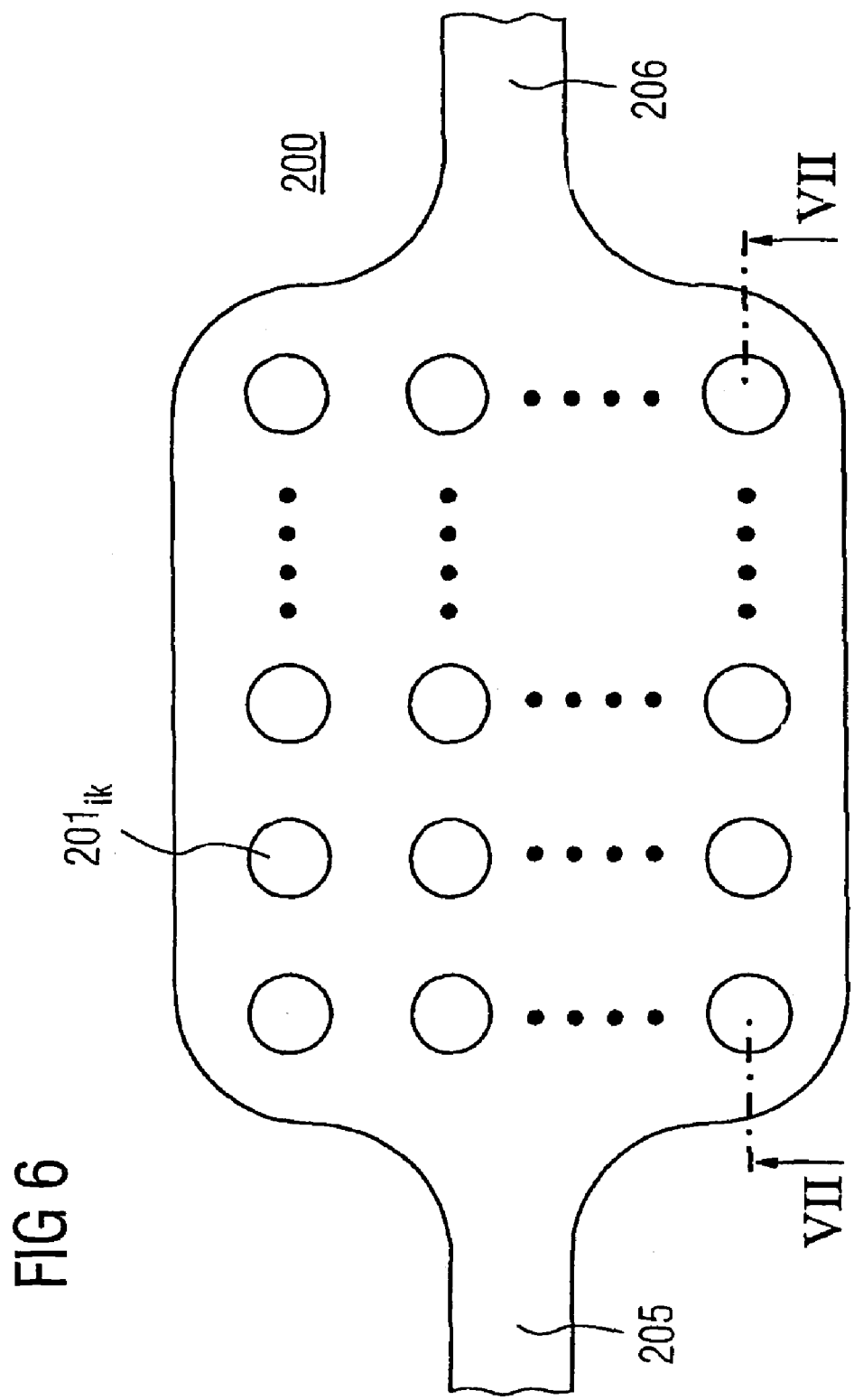
FIG. 6 shows a plan view of an array arrangement for carrying out a PCR simultaneously on different DNAs and FIG. 7 to FIG. 9 respectively show a longitudinal section through FIG. 6 along the line VII-VII in three different function steps.

FIG. 6 depicts an arrangement for carrying out the PCR as an array. Thus, instead of a single PCR cavity, for example the cavity 20 in FIGS. 1 to 5, there are now individual PCR cavities $201_{ik}$ in a closed volume 200, the indices satisfying: i=1 to m and k=1 to n. The chamber 200 has an inlet 205 and an outlet 206, which serve respectively as a feed and discharge for solvent.

Figure 7:
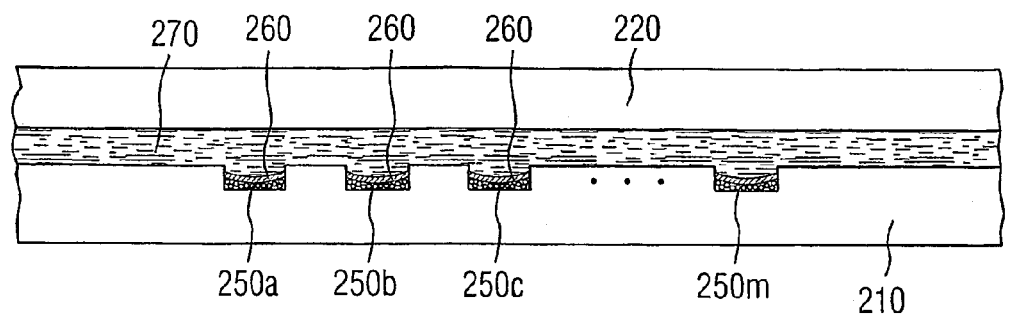

The chamber 200 of FIG. 6 includes the base body 210 with cavities $201_{ik}$ distributed as an array, a row n of which being illustrated in FIG. 7. There is furthermore a lid 220, with which the individual PCR cavities $201_{ik}$ can respectively be closed separately from one another.

The individual PCR cavities $201_{ik}$ are filled in principle according to FIGS. 2 to 5. This is made clear by FIGS. 7 to 9, which depict a row of individual measurement cavities as a section. What is essential here is that a first solid 250a, b, c, . . . is introduced into the measurement cavities corresponding to a row, this solid as a dry reagent respectively being specific for a particular DNA. There is a sealing medium 260 on top of the solids 250a, b, c . . . . A DNA mixture 270 to be studied is supplied in solution or as a suspension via the feed 205.

Figure 8:
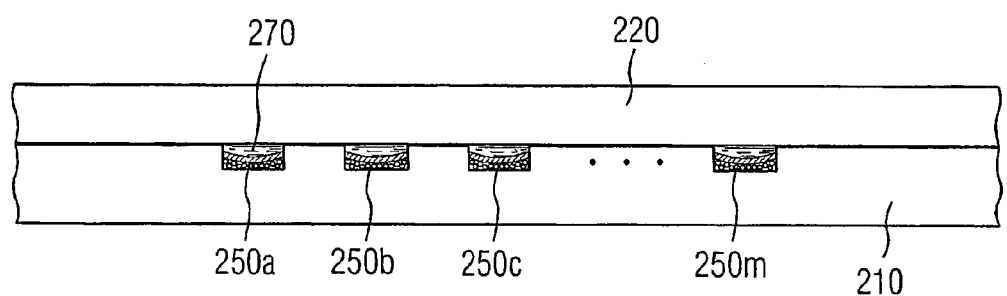
Figure 9:
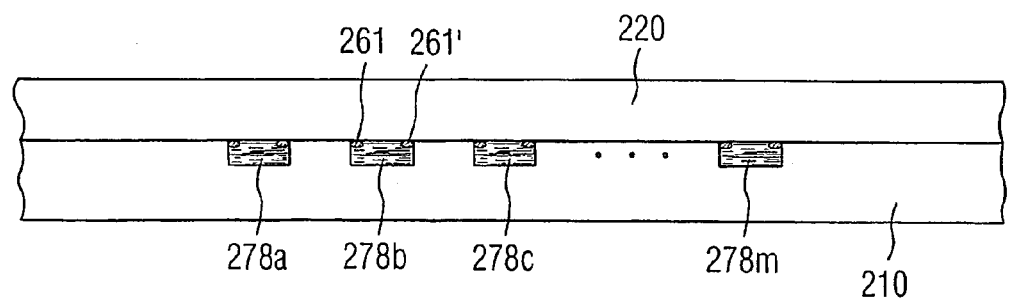

FIG. 8 shows that the lid 220 is closed after the solvent is supplied to the individual measurement cavities $201_{ik}$, so that the individual PCR cavities are now separated. When thermocycling is then carried out according to FIG. 9 with the lid closed, the individual PCR cavities now respectively contain different reagents specific for the amplification of a target DNA, together with the sample DNA. A plurality of PCR reactions can thus be carried out simultaneously and in parallel for a multiplicity of DNAs to be analyzed.

A PCR array according to FIG. 6 may be integrated into an analysis unit according to FIG. 1. Each PCR cavity may additionally be equipped with a sensor device for detecting the PCR product, e.g. with a noble metal electrode for electrical detection. The electrodes may furthermore be equipped with hybridization probes or with PCR primers. This provides improved application possibilities, e.g. the analysis of complex DNA mixtures, which cannot be achieved by multiplex PCR in a single PCR vessel.

The following measures or features are essential in the process as described above and the associated arrangements:
- substrates—with DNA-binding properties, e.g. DNA-binding magnet beads, are introduced in the microchannel or microcavity;
- the lysis reagent and magnet beads may be contained together in a single matrix;
- an input port for whole blood samples is provided;
- means for supplying water are provided, e.g. a feed port for connection to an external water supply;
- a defined ionic strength prevails after supplying water in the microchannel or microcavity with the dry buffer substances;
- means are provided for mixing a whole blood sample and water, or a buffer solution;
- means are provided so that blood, or a blood/water, blood/buffer mixture can flow through the microchannel or microcavity coated with lysis/bead reagent;
- means are provided for generating a magnetic field to fix the DNA/magnet bead complex in the PCR cavity;
- means for closing the PCR cavity are provided;
- thermocycling means are provided for the PCR;
- the PCR cavity has means for at least partial pressure equilibration.

Essential advantages of the arrangement and the process are:
- precise dosing of the PCR reagent takes place directly when producing the cartridge;
- a precise quantity and composition of the PCR reagent is obtained during operation when the PCR cavity is filled or flowed through. No variations are therefore encountered from the setpoint reagent concentration, in particular dilution effects;
- the volume of the PCR cavity when filling is constant and known;
- dry PCR reagent is combined with the solvent, particularly water or water with a low salt content, after the paraffin separating layer is melted, and a defined PCR reagent solution can be created by convection;
- in combination with the binding of DNA to beads (bead technique) the DNA does not have to be additionally eluted outside the PCR cavity.

This ensures that the entire analysis process, including the sample preparation, takes place in the closed system constituted by a disposable cartridge.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A process for DNA amplification by PCR with thermocycling of substances containing the DNA together with associated water-soluble reagents, the process comprising:
   integrating materials in a closed analysis unit including a single-use cartridge with at least one of microchannels and microcavities, in which at least the water-soluble reagents necessary for the PCR are held in a form which is stable when stored at room temperature, and in which the water-soluble reagents are collectively arranged in a layer;
   providing a covering layer, consisting essentially of a water-insoluble medium, in the single-use cartridge, wherein the water-insoluble medium is paraffin;
   covering the layer of water-soluble reagents with the covering layer;
   supplying the DNA to be amplified in an aqueous solvent, wherein the covering effect of the water-insoluble medium is subsequently negated, so that the water-soluble reagents dissolve in the aqueous solvent; and
   performing PCR thermocycling reactions on the aqueous solvent including the DNA to be amplified.

2. The process as claimed in claim 1, wherein water-free substances, storable for several months at room temperature and which make it possible to carry out a PCR after supplying water, are used as reagents for the PCR.

3. The process as claimed in claim 1, wherein for DNA bound in biological structures, disintegration of the biological structures is integrated with the PCR.

4. The process as claimed in claim 1, wherein an analysis unit including a compact cartridge geometry is used.

5. The process as claimed in claim 1, wherein a disposable product is used as the analysis unit for performing the reactions.

6. The process as claimed in claim 1, wherein the PCR reactions are carried out in parallel for different DNA amplifications in an array arrangement, optionally with different primers.

7. The process as claimed in claim 6, wherein PCR reagents with different compositions are used for the different DNA amplifications.

8. The process as claimed in claim 6, wherein the array is filled with a DNA sample, wherein a lid closes the microcavities and isolates them fluidically from one another, and wherein layers of the paraffin are melted and individual DNA amplifications are carried out in parallel.

9. The process as claimed in claim 2, wherein the PCR reactions are carried out in parallel for different DNA amplifications in an array arrangement, optionally with different primers.

10. The process as claimed in claim 9, wherein PCR reagents with different compositions are used for the different DNA amplifications.

11. The process as claimed in claim 9, wherein the array is filled with a DNA sample, wherein a lid closes the microcavities and isolates them fluidically from one another, and wherein layers of the paraffin are melted and individual DNA amplifications are carried out in parallel.

12. The process as claimed in claim 1, wherein the water-soluble reagents are stored in a solid form.

13. The process as claimed in claim 1, wherein a single boundary interface is formed between the covering layer and the layer of the water-soluble reagents.

14. The process as claimed in claim 1, wherein some of the water-soluble reagents are on a surface of the layer of water-soluble reagents, and are interposed between others of the water-soluble reagents within the layer of water-soluble reagents and the covering layer.

15. The process as claimed in claim 1, wherein the covering layer, consisting essentially of a water-insoluble medium, is provided in one of the microcavities of the single-use cartridge.

\* \* \* \* \*